United States Patent [19]
Kim et al.

[11] Patent Number: 5,880,252
[45] Date of Patent: Mar. 9, 1999

[54] PYRROLIDONYL-CONTAINING POLYESTERS AND POLYAMIDES

[75] Inventors: Son Nguyen Kim, Hemsbach; Jörg Breitenbach, Linz; Axel Sanner, Frankenthal; Peter Hössel, Schifferstadt; Siegfried Lang, Ludwigshafen, all of Germany

[73] Assignee: BASF Aktiengesellschaft, Ludwigshafen, Germany

[21] Appl. No.: 619,731

[22] PCT Filed: Sep. 20, 1994

[86] PCT No.: PCT/EP94/03141

§ 371 Date: Mar. 22, 1996

§ 102(e) Date: Mar. 22, 1996

[87] PCT Pub. No.: WO95/09194

PCT Pub. Date: Apr. 6, 1995

[30] Foreign Application Priority Data

Sep. 30, 1993 [DE] Germany ............... 43 33 238.2

[51] Int. Cl.$^6$ .................................. C08G 73/00
[52] U.S. Cl. .............. 528/332; 528/59; 528/63; 528/66; 528/170; 528/183; 528/192; 528/220; 528/229; 528/272; 528/288; 528/310; 528/322; 528/324; 528/339; 528/345; 252/8.84; 252/186.26; 252/304; 252/367.1; 424/70.1; 428/395
[58] Field of Search .................. 528/183, 322, 528/324, 220, 229, 192, 345, 332, 339, 310, 272, 288, 59, 63, 66, 170; 424/70.1; 428/395; 525/178, 183; 252/8.84, 186.26, 304, 367.1

[56] References Cited

U.S. PATENT DOCUMENTS

| | | | |
|---|---|---|---|
| 2,993,021 | 7/1961 | Bavley et al. | 528/345 |
| 4,418,189 | 11/1983 | Morello | 528/345 |

OTHER PUBLICATIONS

*Israel Journal of Chemistry*, vol. 10, 1972, pp. 949–957.

Primary Examiner—P. Hampton-Hightower
Attorney, Agent, or Firm—Keil & Weinkauf

[57] ABSTRACT

Pyrrolidonyl-containing polyesters and polyamides I to III

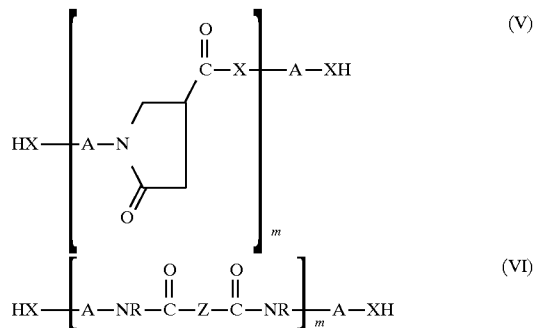

where R, X, A and Z are defined herein, are suitable as film formers and conditioners in hair-cosmetic formulations, for stabilizing hydrogen-peroxide in aqueous solution, for complexing iodine, as tablet binders and as a constituent of film coatings in pharmaceutical preparations, for enzyme and bleach stabilization in detergent formulations, as an auxiliary in the production and finishing of textiles, as a solubilizer and protective colloid in the preparation and stabilization of polymer dispersions, and as an adhesive raw material.

15 Claims, No Drawings

PYRROLIDONYL-CONTAINING POLYESTERS AND POLYAMIDES

The present invention relates to novel pyrrolidonyl-containing polyesters and polyamides, to processes for their preparation, and to the use of these pyrrolidonyl-containing polyesters and polyamides in specific industrial areas.

Polyvinylpyrrolidone (PVP) and copolymers of vinyl pyrrolidone prepared by means of free radicals, for example using vinyl acetate, have hitherto found use in various industrial areas. In particular, their properties are utilized as complexing agents, film-forming agents, depot formers, enzyme supports, binders and adhesive raw materials. The applications are in the cosmetics and pharmaceuticals sectors and in the foodstuffs, textiles, detergents and not least in the polymers areas, for example as solubilizers or protective colloids.

However, PVP and copolymers thereof have a number of drawbacks in these applications, in particular their unsatisfactory biodegradability or eliminability, their toxicity potential (monomeric vinyl pyrrolidone has been classified as carcinogenic in animal experiments) and in some cases their incompatibility with certain saccharides (for example in mixtures of PVP with maltodextrins). In addition, the applicational properties of PVP and copolymers thereof are frequently also unsatisfactory.

U.S. Pat. No. 2,993,021 (1) discloses polyesters obtained by polycondensation of bispyrrolidone derivatives of the structure

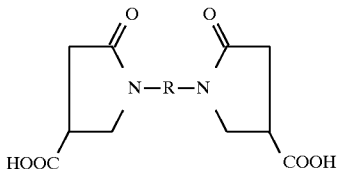

where R is an alkylene, oxaalkylene, thiaalkylene or azaalkylene bridge having 2 to 12 carbon atoms, for example 1,2-ethylene or 1,3-propylene, with a polyhydroxyl compound, for example ethylene glycol or propylene glycol. These polyesters are suitable, under certain circumstances, as plasticizers for plastics and for the preparation of alkyd resins, which, as is known, play an important role as vehicles in the paints industry.

The Israel Journal of Chemistry, Vol. 10 (1972), 949–957 (2) discloses highly heat-resistant polyamides prepared by reacting aromatic diamines, such as benzidine, 4,4'-diaminodiphenyl sulfone, 4,4'-diaminodiphenyl ether or p-phenylenediamine, with bispyrrolidonedicarboxylic acids obtained by reacting itaconic acid with said aromatic diamines. These polyamides apparently have low solubility, since they only dissolve in concentrated sulfuric acid and some partially dissolve in dimethylformamide or dimethyl sulfoxide. A suggested use is in adhesive formulations.

It is an object of the present invention to provide novel materials as replacement for PVP and copolymers thereof in said areas of application which do not have the disadvantages of the prior art.

We have found that this object is achieved by pyrrolidonyl-containing polyesters and polyamides of the formulae I to III

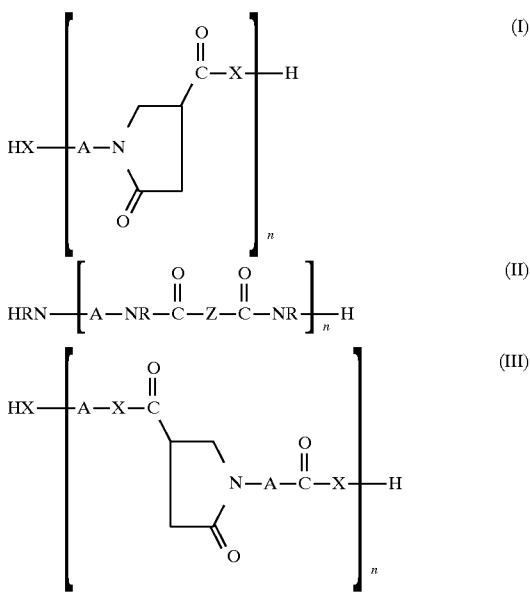

where

R is hydrogen or $C_1$- to $C_4$-alkyl, where two radicals R can be linked to one another to form a six-membered ring, X is oxygen or —NR—, A is $C_1$- to $C_{20}$-alkylene, which can be interrupted by one or more non-adjacent oxygen atoms, sulfur atoms or functional groups —NR—, where the nitrogen atom can be protonated or quaternized, —CO—, —CO—O—, —CO—NR—, —SO— or $SO_2$—, and which may carry additional functional groups —COOH or —$SO_3H$, $C_6$- to $C_{20}$-cycloalkylene, $C_6$- to $C_{20}$-arylene, which may be interrupted by oxygen, sulfur or —NR—, —SO— or —$SO_2$— and may additionally carry functional groups —COOH or —$SO_3H$, or a mixture of such groups, Z is a group of the formula IV

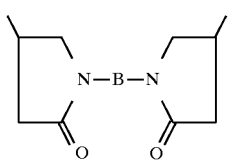

where B is $C_1$- to $C_{20}$-alkylene, which may be interrupted by one or more non-adjacent oxygen atoms, sulfur atoms or functional groups —NR—, where the nitrogen atom may be protonated or quaternized, —CO—, —CO—O—, —CO—O—, —CO—NR—, —SO— or —$SO_2$—, and which may carry additional functional groups —COOH or —$SO_3H$, $C_6$- to $C_{20}$-cycloalkylene or a mixture of such groups, or is a mixture of groups of the formula IV with groups A, and n is a number from 5 to 500.

$C_1$- to $C_4$-alkyl $R^1$ is ethyl, n-propyl, isopropyl, n-butyl, isobutyl, sec-butyl, tert-butyl or, in particular, methyl. If two —NR— groups are linked to one another by a $C_1$- to $C_3$-alkylene group, the two radicals R can also be linked to one another to form a saturated six-membered ring containing two nitrogen atoms, in particular a piperazine ring.

The following are examples of the bridge A and the bridge B (where the latter cannot contain aromatic rings): methylene 1,2-ethylene, if desired incorporated into a piperazine ring
1,3-propylene
1,2-propylene
1,4-butylene
2,3-butylene
pentamethylene (for example formed from ε-caprolactam)
hexamethylene
2,5-hexylene
heptamethylene
octamethylene
2,7-octylene
nonamethylene
decamethylene
dodecamethylene
tetradecamethylene
hexadecamethylene
octadecamethylene
eicosamethylene
—CH$_2$—O—CH$_2$
—CH$_2$CH$_2$—O—CH$_2$CH$_2$—
—CH$_2$CH$_2$—O—CH$_2$CH$_2$—O—CH$_2$CH$_2$—
—CH$_2$CH$_2$—O—CH$_2$CH$_2$—O—CH$_2$CH$_2$—O—CH$_2$CH$_2$—
—CH$_2$CH$_2$CH$_2$—O—CH$_2$CH$_2$—O—CH$_2$CH$_2$CH$_2$—
—CH$_2$CH$_2$—S—CH$_2$CH$_2$—
—CH$_2$CH$_2$CH$_2$—S—CH$_2$CH$_2$CH$_2$—
—CH$_2$CH$_2$CH$_2$—S—S—CH$_2$CH$_2$CH$_2$—
—CH$_2$CH$_2$CH$_2$—S—CH$_2$CH$_2$—S—CH$_2$CH$_2$CH$_2$—
—CH$_2$CH$_2$—NH—CH$_2$CH$_2$—
—CH$_2$CH$_2$—N(CH$_3$)—CH$_2$CH$_2$—

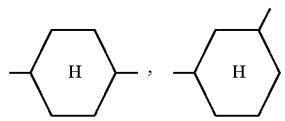 (as part of a piperazine ring)

—CH$_2$CH$_2$—NH—CH$_2$CH$_2$—NH—CH$_2$CH$_2$—
—CH$_2$CH$_2$CH$_2$—NH—NH—CH$_2$CH$_2$CH$_2$—
—CH$_2$—CO—CH$_2$—
—CH$_2$—CO—CH$_2$CH$_2$—
—CH$_2$CH$_2$—CO—CH$_2$CH$_2$—
—CH$_2$—CO—O—CH$_2$—
—CH$_2$—CO—O—CH$_2$CH$_2$—
—CH$_2$—CO—NH—CH$_2$—
—CH$_2$—CO—N(CH$_3$)—CH$_2$—
—(CH$_2$)$_4$—CO—NH—(CH$_2$)$_6$— (for example formed from hexamethylenediamine adipate)
—CH$_2$—SO—CH$_2$—
—CH$_2$—SO$_2$—CH$_2$—
—CH(COOH)—
—CH(CH$_2$COOH)—
—CH(CH$_2$CH$_2$COOH)— (from glutamic acid)
—CH(SO$_3$H)—
—CH(CH$_2$SO$_3$H)—

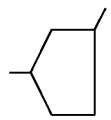

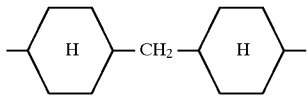

-continued

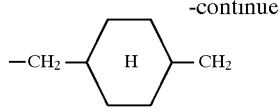

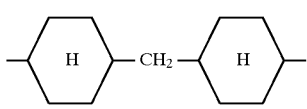

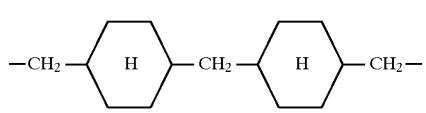

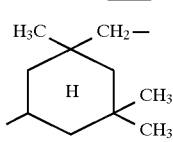

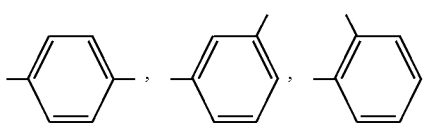

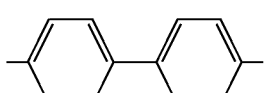

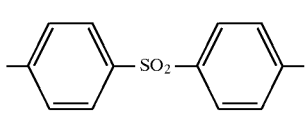

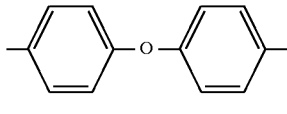

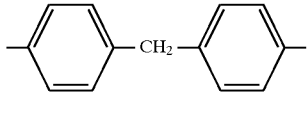

A and B preferably have the following meanings:
1,2-ethylene, if desired incorporated into a piperazine ring
1,3-propylene
1,2-propylene
1,4-butylene
pentamethylene (for example from ε-caprolactam)
hexamethylene
octamethylene

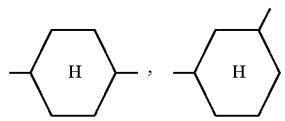 (as part of a piperazine ring)

—(CH$_2$)$_4$—CO—NH—(CH$_2$)$_6$— (for example formed from hexamethylenediamine adipate)
—CH(CH$_2$CH$_2$COOH)— (from glutamic acid)

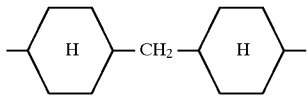

The bridges A and B in the novel polyesters and polyamides I to III can also be mixtures of more than one, in particular from 2 to 3, different groups of this type. The individual species here are generally distributed more or less randomly, since the polycondensates I to III are in such a case usually prepared by reaction with mixtures of the corresponding aminoalcohols, diamines or aminocarboxylic acids. If the formulae I to III contain more than one bridge A, the latter can be identical or different.

Quaternizing agents for tertiary nitrogen atoms in the bridges A and B can be, for example, alkyl halides or dialkyl sulfates, such as methyl chloride, ethyl chloride, methyl bromide, ethyl bromide, benzyl chloride, dimethyl sulfate or diethyl sulfate. —NR— groups in the bridges A and B can be protonated, in particular, using organic acids, for example lactic acid.

In order to modify the polycondensates II, some, in particular up to 30 mol %, of the bispyrrolidone structures IV can, if desired, be replaced by bridges formed from dicarboxylic acids of the formula HOOC—A—COOH. In such a case, preference is given to aromatic dicarboxylic acids, which can also carry sulfo groups in order to increase their water solubility, for example terephthalic acid, 2-sulfoterephthalic acid, isophthalic acid, 5-sulfoisophthalic acid, phthalic acid, sulfophthalic acids, naphthalenedicarboxylic acids or sulfonaphthalenedicarboxylic acids. The sulfodicarboxylic acids are normally employed as alkali metal or ammonium sulfonates.

The degree of polycondensation n is preferably from 10 to 400, in particular from 15 to 300. The polyesters and polyamides I to III usually have K values of from 5 to 50, in particular from 9 to 40, measured as a 0.1% strength by weight solution in N-methylpyrrolidone.

The present invention also relates to processes for the preparation of novel polyesters and polyamides I to III.

Pyrrolidonyl-containing polyesters and polyamides I are expediently prepared by reacting itaconic acid, itaconic anhydride, an itaconic ester or an itaconyl halide with an aminoalcohol or diamine of the formula HX—A—NH$_2$ in a molar ratio of approximately 1:1, and polycondensing the resultant monomeric pyrrolidone derivative at elevated temperature.

Pyrrolidonyl-containing polyamides II are expediently prepared by reacting itaconic acid, itaconic anhydride, an itaconic ester or an itaconyl halide with a diamine of the formula H$_2$N—B—NH$_2$ in a molar ratio of approximately 2:1, and polycondensing the resultant monomeric bispyrrolidone derivative or a mixture thereof with a dicarboxylic acid or dicarboxylic acid derivative of the formula Y—CO—A—CO—Y, where each Y, independently of the others, is OH, O-alkyl, for example O—C$_1$— to C$_4$-alkyl, or halogen, for example Cl or Br, with a diamine of formula HRN—A—NRH at elevated temperature.

Pyrrolidonyl-containing polyesters and polyamides III are expediently prepared by reacting itaconic acid, itaconic anhydride, an itaconic ester or an itaconyl halide with an aminocarboxylic acid of the formula H$_2$N—A—CO—Y, where Y is OH, O-alkyl, for example O—C$_1$- to C$_4$-alkyl, or halogen, for example Cl or Br, in a molar ratio of approximately 1:1, and polycondensing the resultant monomeric pyrrolidone derivative with a diol or diamine of the formula HX—A—XH at elevated temperature.

Suitable starting materials are in particular itaconic acid itself, but also derivatives thereof, such as its dimethyl or diethyl ester or its dichloride.

The reaction of itaconic acid or derivatives thereof with monomeric compounds containing primary amino groups to give pyrrolidone structures is known in principle. The reaction is advantageously carried out under an inert-gas atmosphere, for example under nitrogen, in a solvent, preferably water, and at from about 90° to 120° C.

The subsequent polycondensation reaction in order to produce the polyesters and polyamides I to III is generally at from 100° to 300° C., in particular at from 150° to 250° C. Solvent from the first step, for example water, is expediently removed in advance, for example by distillation. Water formed during the polycondensation, which is usually formed as steam, is likewise expediently removed, either continuously during polycondensation or subsequently thereto. The reaction is carried out at atmospheric pressure, expediently under an inert-gas atmosphere, or at superatmospheric pressure, for example at up to 25 bar. The reaction is generally complete within 2 to 10 hours.

The polycondensation reaction can be accelerated by using catalysts in the conventional amounts for this purpose. Suitable catalysts here are in particular mineral acids or acidic salts of mineral acids, for example orthophosphoric acid, alkali metal dihydrogenphosphates or alkali metal hydrogensulfates. Heavy-metal salts of fatty acids, such as tin octanoate, can also be employed for this purpose. The acidic catalysts remaining in the product can be neutralized using conventional bases.

The present invention also relates to pyrrolidonyl-containing polyurethanes or polyureas and pyrrolidonyl-containing polycarboxylates obtainable by reacting pyrrolidonyl-containing polyesters or polyamides of the formulae V to VII

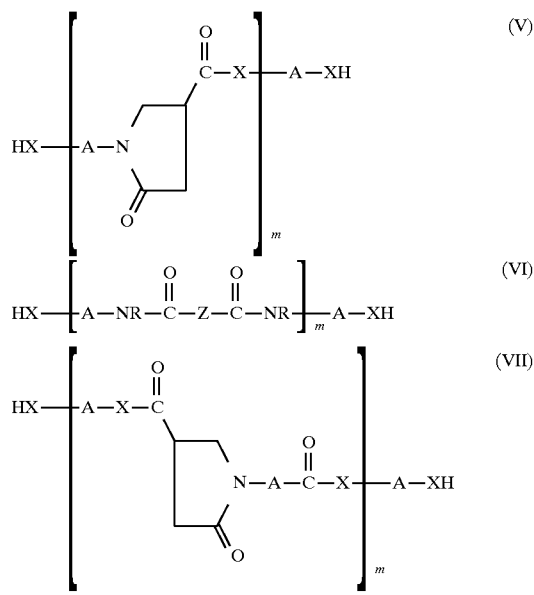

where

R is hydrogen or C$_1$- to C$_4$-alkyl, where two radicals R can be linked to one another to form a six-membered ring, X is oxygen or —NR—, A is C$_1$- to C$_{20}$-alkylene, which can be interrupted by one or more non-adjacent oxygen atoms, sulfur atoms or functional groups —NR—, where the nitrogen atom can be protonated or quaternized, —CO—, —CO—O—, —CO—NR—, —SO— or SO$_2$—, and which may carry additional functional groups —COOH or —SO$_3$H, C$_6$- to C$_{20}$-cycloalkylene, C$_6$- to C$_{20}$-arylene, which may be interrupted by oxygen, sulfur or —NR—, —SO— or —SO$_2$— and may additionally carry functional groups —COOH or —SO$_3$H, or a mixture of such groups, Z is a group of the formula VIII

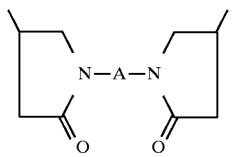

or a mixture of groups of formula VIII with group A and
m is a number from 1 to 50,
with diisocyanates of the formula OCN—D—NCO, where D is $C_2$- to $C_8$-alkylene, $C_5$- to $C_{10}$-cycloalkylene, phenylene or $C_1$- to $C_4$-alkylphenylene, or dianhydrides of the formula

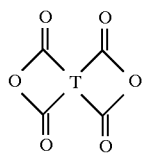

where T is a tetravalent radical of a $C_2$- to $C_6$-alkane, of a $C_5$- to $C_{10}$-cycloalkane, of benzene or of naphthalene.

If the formulae V to VII contain more than one bridge A, the latter may be identical or different.

The compounds V are expediently prepared by reacting itaconic acid, itaconic anhydride, an itaconic ester or an itaconyl halide with a slight excess of an aminoalcohol or diamine of the formula HX—A—$NH_2$ or by subsequently adding as excess a small to molar amount of another aminoalcohol or diamine HX—A—$NH_2$ or of a diol of the formula HO—A—OH and allowing this to react, and, if desired, polycondensing the mixture at elevated temperature to a degree of polycondensation m, so that free amino or hydroxyl groups which are capable of reacting with diisocyanate or dianhydride are at both ends of the polycondensate chain.

The compounds VI are expediently prepared by reacting itaconic acid, itaconic anhydride, an itaconic ester or an itaconyl halide with an aminoalcohol or diamine of the formula HX—A—$NH_2$ in a molar ratio of approximately 2:1, then reacting the product with a small to molar amount of the same or another aminoalcohol or diamine HX—A—$NH_2$ or of a diol of the formula HO—A—OH, and, if desired, polycondensing the product with the same or another amonoalcohol or diamine HX—A—$NH_2$ at elevated temperature to the degree of polycondensation m, so that free amino or hydroxyl groups which are capable of reacting with diisocyanate or dianhydride are at both ends of the polycondensate chain. Some of the bispyrrolidonedicarboxylic acid units can be replaced by dicarboxylic acids of the formula HOOC—A—COOH.

The compounds VII are expediently prepared by reacting itaconic acid, itaconic anhydride, an itaconic ester or an itaconyl halide with an aminocarboxylic acid of the formula $H_2$N—A—CO—Y, where Y is OH, O-alkyl, for example O—$C_1$- to $C_4$-alkyl, or halogen, for example Cl or Br, in a molar ratio of approximately 1:1, then reacting the product with a small to molar amount of an aminoalcohol or diamine of the formula HX—A—$NH_2$ or of a diol of the formula HO—A—OH, and, if desired, polycondensing the product with the same or another aminoalcohol or diamine HX—A—$NH_2$ at elevated temperature to the degree of polycondensation m, so that the amino or hydroxyl groups which are capable of reacting with diisocyanate or dianhydride are at both ends of the polycondensation chain.

Suitable diisocyanates OCN—D—NCO are $C_2$- to $C_8$-alkylene diisocyanates, for example 1,2-ethylene diisocyanate, 1,4-butylene diisocyanate, hexamethylene diisocyanate or octamethylene diisocyanate, $C_5$- to $C_{10}$-cycloalkylene diisocyanates, for example 1,3-cyclopentylene diisocyanate, 1,3- or 1,4-cyclohexylene diisocyanate or isophorone diisocyanate, o-, m- or p-phenylene diisocyanate or ($C_1$- to $C_4$-alkyl)phenylene diisocyanates, for example tolylene diisocyanate.

The tetravalent radical T in the dianhydrides used is, for example, 1,1,2,2-substituted ethane, 1,2,3,4-substituted butane, 1,2,3,4- or 1,2,4,5-substituted cyclohexane, 1,2,3,4- or 1,2,4,5-substituted benzene or 1,2,3,4- or 2,3,6,7-substituted naphthalene.

The reaction to give the novel pyrrolidonyl-containing polyurethanes or polyureas and the novel pyrrolidonyl-containing polycarboxylates is carried out by methods known per se and therefore requires no further explanation.

The novel pyrrolidonyl-containing polyurethanes and polyureas and the novel pyrrolidonyl-containing polycarboxylates are in principle suitable for the same applications as the novel pyrrolidonyl-containing polyesters and polyamides of the formulae I to III described above.

The present invention furthermore relates to the use of pyrrolidonyl-containing polyesters and polyamides containing at least one structural unit of the formula IX

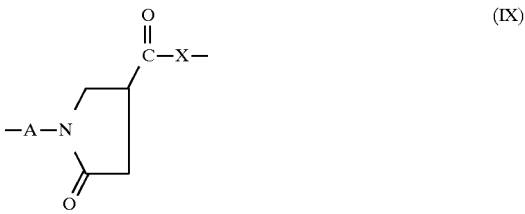

where
X is oxygen or —NR—,
R is hydrogen or $C_1$- to $C_4$-alkyl, where two radicals R can be linked to one another to form a six-membered ring,
A is $C_1$- to $C_{20}$-alkylene, which can be interrupted by one or more non-adjacent oxygen atoms, sulfur atoms or functional groups —NR—, where the nitrogen atom can be protonated or quaternized, —CO—, —CO—O—, —CO—NR—, —SO— or —$SO_2$—, and which may carry additional functional groups —COOH or —$SO_3H$, $C_6$- to $C_{20}$-cycloalkylene, $C_6$- to $C_{20}$-arylene, which may be interrupted by oxygen, sulfur or —NR—, —SO— or —$SO_2$— and may additionally carry functional groups —COOH or —$SO_3H$, or a mixture of such groups,
as film-forming agents and conditioners in hair cosmetic formulations.

Preferred pyrrolidonyl-containing polyesters and polyamides are those of the formulae I to III, where —NR— in the formula II can also be replaced by oxygen, and the products of the reaction of compounds of the formulae V to VII with diisocyanates of the formula OCN—D—NCO or dianhydrides of the formula

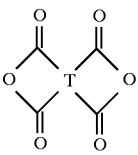

The pyrrolidonyl-containing polyesters and polyamides described have excellent applicational properties as film-forming agents in hair sprays, hair foams, hair-setting compositions or hair gels and as conditioners in hair-care rinses or hair shampoos. They are generally readily water- or alcohol-soluble, and their viscosity is significantly lower than that of comparable known compositions.

The present invention furthermore relates to the use of pyrrolidonyl-containing polyesters and polyamides containing at least one structural unit IX for stabilizing hydrogen peroxide in aqueous solution.

Accordingly, the present invention also relates to complexes of hydrogen peroxide and these pyrrolidonyl-containing polyesters or polyamides which preferably contain from 0.5 to 35% by weight, in particular from 5 to 18% by weight, of $H_2O_2$.

Preferred pyrrolidonyl-containing polyesters and polyamides here are those of the formulae I to III, where —NR— in the formula II can also be replaced by oxygen, and the products of the reaction of the compounds of the formulae V to VII with diisocyanates of the formula OCN—D—NCO or dianhydrides of the formula

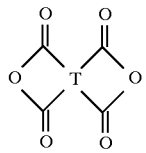

Said hydrogen peroxide/polyester and polyamide complexes have a significantly improved stabilization behavior in aqueous solution than does PVP, in particular in the temperature range from 60° to 90° C. While a decomposition of approx. 20% has been observed for 0.2% by weight technical-grade hydrogen peroxide over 9 hours at 80° C., this figure is approx. at 8% for PVP and about 2% for the polyamides or polyesters described. In addition, the stabilization is successful if decomposition of the hydrogen peroxide at elevated temperature is additionally accelerated by relatively high pH values. At pH 9 (60° C., 6 ppm of copper ions), 99.4% of the initial hydrogen peroxide has decomposed after 45 minutes, whereas, under the same conditions, only 30% of the hydrogen peroxide has decomposed with the polyamides or polyesters described, but 58% with PVP.

Solid polycondensate/hydrogen peroxide complexes containing 33% by weight of hydrogen peroxide, based on the total solids content, can also be prepared from the solutions. The stabilizing effect is achieved even if only small amounts (from 1 to 30%) of the pyrrolidone units are introduced into a polyamide or a polyester. Solutions of the polyamide or polyester and hydrogen peroxide, preferably in water, are evaporated to dryness or solid polyamide or polyester is sprayed with a hydrogen peroxide solution in a fluidized-bed process and subsequently dried. The decomposition amounts to 25% over 10 hours at 50° C., while 40% of a conventional urea/hydrogen peroxide complex decomposes under the same conditions.

The hydrogen peroxide complexes described can be used, for example, in toothpastes, in acne therapy, in disinfectants, in wound dressings, in hair cosmetics (hair coloring) or as the solid component for chemical reactions, such as polymerizations or oxidations.

The present invention furthermore relates to the use of pyrrolidonyl-containing polyesters and polyamides containing at least one structural unit IX for complexing iodine.

Accordingly, the present invention relates to complexes of iodine and these pyrrolidonyl-containing polyesters and polyamides which preferably contain from 2 to 20% by weight, in particular from 5 to 14% by weight, especially from 6 to 12% by weight, of iodine.

Preferred pyrrolidonyl-containing polyesters and polyamides here are those of the formulae I to III, where —NR— in the formula II can also be replaced by oxygen, and the products of the reaction of the compounds of the formulae V to VII with diisocyanates of the formula OCN—D—NCO or dianhydrides of the formula

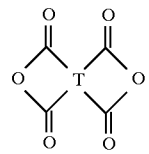

Polymer/iodine complexes of this type are particularly suitable as fine disinfectants in the medical sector. The novel complexes of iodine and, if desired, iodides, such as potassium iodide, and other oxidants and the pyrrolidonyl-containing polyesters and polyamides described are at least equal to the known PVP/iodine complexes in their application properties.

The present invention furthermore relates to the use of pyrrolidonyl-containing polyesters and polyamides containing at least one structural unit IX as tablet binders and as a constituent of film coatings in pharmaceutical preparations.

Preferred pyrrolidonyl-containing polyesters and polyamides here are those of the formulae I to III, where —NR— in the formula II can also be replaced by oxygen, and the products of the reaction of the compounds of the formulae V to VII with diisocyanates of the formula OCN—D—NCO or dianhydrides of the formula

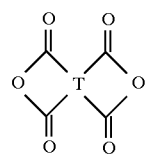

The present invention furthermore relates to the use of pyrrolidonyl-containing polyesters and polyamides containing at least one structural unit IX for enzyme stabilization and for bleach stabilization in detergent formulations.

Preferred pyrrolidonyl-containing polyesters and polyamides here are those of the formulae I to III, where —NR— in the formula II can also be replaced by oxygen, and the products of the reaction of the compounds of the formulae V to VII with diisocyanates of the formula OCN—D—NCO or dianhydrides of the formula

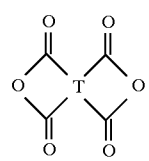

The present invention furthermore relates to the use of pyrrolidonyl-containing polyesters and polyamides containing at least one structural unit IX as auxiliaries in the production and finishing of textiles.

Preferred pyrrolidonyl-containing polyesters and polyamides here are those of the formulae I to III, where —NR— in the formula II can also be replaced by oxygen, and the products of the reaction of the compounds of the formulae V to VII with diisocyanates of the formula OCN—D—NCO or dianhydrides of the formula

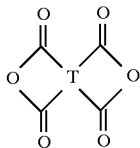

The present invention furthermore relates to the use of pyrrolidonyl-containing polyesters and polyamides containing at least one structural unit IX as solubilizers and protective colloids in the preparation and stabilization of polymer dispersions.

Preferred pyrrolidonyl-containing polyesters and polyamides here are those of the formulae I to III, where —NR— in the formula II can also be replaced by oxygen, and the products of the reaction of the compounds of the formulae V to VII with diisocyanates of the formula OCN—D—NCO or dianhydrides of the formula

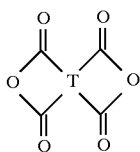

The present invention furthermore relates to the use of pyrrolidonyl-containing polyesters and polyamides containing at least one structural unit of the formula X

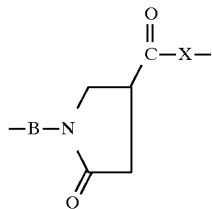

where
X is oxygen or —NR—,
R is hydrogen or $C_1$- to $C_4$-alkyl, where two radicals R can be linked to one another to form a six-membered ring, and
B is $C_1$- to $C_{20}$-alkylene, which can be interrupted by one or more non-adjacent oxygen atoms, sulfur atoms or functional groups —NR— where the nitrogen atom can be protonated or quaternized, —CO—, —CO—O—, —CO—NR—, —SO— or —SO$_2$—, and may carry additional functional groups —COOH or —SO$_3$H, $C_6$- to $C_{20}$-cycloalkylene or a mixture of such groups,
as adhesives.

Preferred pyrrolidonyl-containing polyesters and polyamides here are those of the formulae I to III, where —NR— in the formula II can also be replaced by oxygen, and the products of the reaction of the compounds of the formulae V to VII with diisocyanates of the formula OCN—D—NCO or dianhydrides of the formula

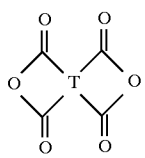

The pyrrolidonyl-containing polyesters and polyamides described, in particular those of the formulae I to III and the products of the reaction of the compounds V to VII with diisocyanates or dianhydrides, have good biodegradability or eliminability since the polymer backbone contains groups which can be readily removed hydrolytically.

The polycondensates described are easy to prepare, and, for example, no organic solvents are needed for their preparation. The starting compound itaconic acid is readily and inexpensively obtainable from sugars or molasses by fermentative processes.

In many applications, the polycondensates described are superior to PVP and copolymers thereof.

PREPARATION EXAMPLES

General Preparation Procedure A

The monomeric pyrrolidone derivative conforming to the formula I is prepared in a known manner from itaconic acid and the aminoalcohol or diamine shown in Table 1 or a mixture of these reactants in water as solvents at approx. 100° C. under a nitrogen atmosphere. Virtually all the water is subsequently removed by distillation, and the polycondensation is effected by heating to approx. 250° C. under atmospheric pressure under a nitrogen atmosphere. Water of condensation formed as steam is continuously removed by passing a stream of nitrogen through the mixture. The reaction is complete after about 6 to 15 hours. The use of a catalyst, such as orthophosphoric acid or sodium dihydrogen phosphate in conventional amounts, reduces the reaction time to from about 3 to 10 hours.

General Preparation Procedure B

The bispyrrolidonedicarboxylic acid of the formula XI

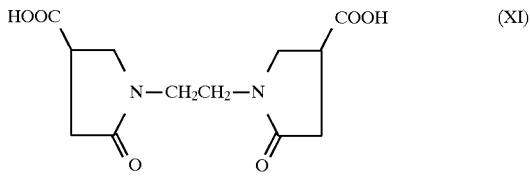

is prepared in a known manner from itaconic acid and ethylenediamine in a molar ratio of 2:1 in water as solvent at approx. 100° C. under a nitrogen atmosphere. Virtually all the water is subsequently removed by distillation, the diamine or mixture of diamines shown in Table 1 and any dicarboxylic acids or aminocarboxylic acids shown in Table 1 are added, and the polycondensation is effected by heating to approx. 250° C. under atmospheric pressure under a nitrogen atmosphere. Water of condensation formed as steam is continuously removed by passing a stream of nitrogen through the mixture. The reaction is complete after from about 6 to 15 hours. The use of a catalyst, such as orthophosphoric acid or sodium dihydrogen phosphate in the conventional amount, reduces the reaction time to from about 3 to 10 hours.

TABLE 1

Composition [molar amount] and K values of the polycondensates prepared

| Example No. | Preparation procedure | Pyrrolidonyl-supplying compound | Aminoalcohol/ diamine | Aminocarboxylic acid | Dicarboxylic acid | K value (0.1% by wt. in NMP) |
|---|---|---|---|---|---|---|
| 1 | A | IA [1] | EA [1] | — | — | 9.6 |
| 2 | A | IA [1] | EDA [4] | — | — | 33.0 |
| 3 | A | IA [1] | AEP [1] | — | — | 24.1 |
| 4 | B | XI [1] | EDA [1] | — | — | 31.3 |
| 5 | B | XI [1] | EDA [0.5], P [0.5] | — | — | 32.2 |
| 6 | B | XI [1] | EDA [0.8], AEP [0.2] | GA [0.3] | — | 29.2 |
| 7 | A | IA [1] | EDA [0.5], DC [0.5] | — | — | 29.9 |
| 8 | B | XI [1] | EDA [0.3], DC [0.7] | — | — | 31.7 |
| 9 | B | XI [1.2] | EDA-[0.3], DC [1.1] | GA [0.3] | — | 22.1 |
| 10 | B | XI [1] | DAP [0.5], DC [0.5] | AH [0.3] | — | 29.2 |
| 11 | B | XI [1] | DAP [0.3], DC [1] AEP [0.2] | — | IPA [0.4] | 22.8 |
| 12 | B | XI [1] | EDA [0.15], DC [1], | — | SIPA [0.1] | 24.3 |

IA = itaconic acid
XI = bispyrrolidonedicarboxylic acid of the formula XI
EA = ethanolamine
EDA = ethylenediamine
AEP = N-(2-aminoethyl)piperazine
P = piperazine
DC = 4,4'-diaminodicyclohexylmethane (dicyhane)
DAP = 1,2-diaminopropane
GA = glutamic acid
AH = AH salt (hexamethylenediamine adipate)
IPA = isophthalic acid
SIPA = 5-sulfoisophthalic acid
NMP = N-methylpyrrolidone

EXAMPLE 13

Preparation of a Pyrrolidonyl-Containing Polyurea 160 g (0.1 mol) of a poly(itaconic acid ethylenediamine) prepared using a slight excess of ethylenediamine were dissolved with stirring at 20° C. in 375 g of a mixture of ethanol and water in a ratio by volume of 4:1. 15.14 g (0.09 mol) of hexamethylene diisocyanate were then added dropwise, with the internal temperature remaining below 30° C. The reaction solution was then stirred at 20° C. for a further 2 hours. The solvent was removed at 70° C. in a vacuum drying cabinet. Drying gave a water-soluble, hard solid. Instead of drying, an aqueous solution of the product was obtainable by adding further water and removing the ethanol by distillation at about 60° C. under slightly reduced pressure.

Application properties in hair cosmetics

The polycondensates from Examples 1 to 6 were investigated for their suitability as hair conditioners. To this end, their solubilities in ethanol and water, their surfactant compatibility and their combability from the hair were determined. The latter determination was carried out using a hair-care rinse of commercial composition containing the polycondensates from Examples 1 to 6.

TABLE 2

Solubilities, surfactant compatibility and combability of the polycondensates from Examples 1 to 6

| Example No. | Solubility (5% strength by wt.) in | | | Surfactant compatibility | Combability | |
|---|---|---|---|---|---|---|
| | Ethanol | Ethanol/ water (1:1) | Water | | wet | dry |
| 1 | 0 | + | + | good | very good | very good |
| 2 | 0 | + | + | good | very good | very good |
| 3 | 0 | + | + | good | good | very good |
| 4 | 0 | + | + | good | very good | very good |
| 5 | 0 | + | 0 | good | very good | very good |

TABLE 2-continued

Solubilities, surfactant compatibility and combability of the polycondensates from Examples 1 to 6

| Example No. | Solubility (5% strength by wt.) in | | | Surfactant compatibility | Combability | |
|---|---|---|---|---|---|---|
| | Ethanol | Ethanol/water (1:1) | Water | | wet | dry |
| 6 | 0 | + | + | good | very good | very good |
| for comparison: | | | | | | |
| PVP-QVI | + | + | 0 | good | good | good |

+ = soluble,
0 = cloudy

In the comparative example, PVP-QVI is a commercially available hair cosmetic polymer made from N-vinylpyrrolidone and vinylimidazolium methochloride.

The surfactant compatibility was determined in 5% strength by weight aqueous solution containing 14% by weight of a commercially available fatty alcohol ether sulfate (Texapon® NSO).

The polycondensates from Examples 7 to 12 were investigated for their suitability as film formers in hair spray and hair-setting formulations. To this end, their solubilities in ethanol and water, the tack and ease of washing out of a film on a glass plate and the curl retention and flexural rigidity of treated hairs were determined.

For the measurement of curl retention and flexural rigidity, an aerosol hair spray formulation having the following composition was employed:

3% by weight of the polycondensate from Examples 7 to 12
52% by weight of ethanol
10% by weight of distilled water
35% by weight of dimethyl ether.

For the production of a film on a glass plate, a formulation having the following composition was employed:

4% by weight of the polycondensate from Examples 7 to 12
32% by weight of ethanol
64% by weight of distilled water.

TABLE 3

Solubilities, tack, ease of washing out, curl retention and flexural rigidity of the polycondensates from Examples 7 to 12

| Ex. No. | Solubility (5 % strength by weight) in | | | Film on glass plate | | Hair treatment | |
|---|---|---|---|---|---|---|---|
| | Ethanol | Ethanol/water (1:1) | Water | Tack [score] | Ease of washing out | Curl retention [%] | Flexural rigidity [g] |
| 7 | D | + | 0 | 4 | good | 17 | 312 |
| 8 | + | + | 0 | 3 | still good | 23 | 230 |
| 9 | 0 | + | 0 | 3 | good | 37 | 215 |
| 10 | + | + | 0 | 1 | good | 18 | 55 |
| 11 | 0 | + | 0 | 1 | good | 41 | 82 |
| 12 | 0 | + | D | 1 | good | 29 | 61 |
| for comp.: | | | | | | | |
| PVP-PVA | + | + | 0 | 5 | good | 35 | 79 |

+ = soluble,
0 = cloudy,
D = dispersion

In the comparative example, PVP-PVA was a commercially available hair-cosmetic polymer comprising 30% by weight of N-vinylpyrrolidone and 70% by weight of vinyl acetate.

In the assessment of tack, 1 (non-tacky) denotes the best score and 5 (tacky) the worst score for hair-cosmetic polymers.

We claim:

1. A pyrrolidonyl-containing polyester or polyamide of the formula III

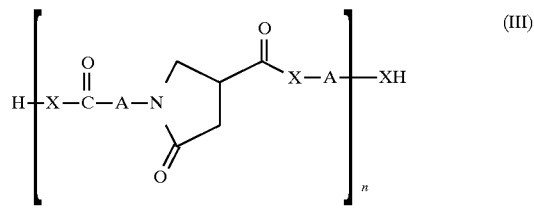

(III)

where

X is oxygen or —NR—,

R is hydrogen, $C_1$- to $C_4$-alkyl, or two radicals R are linked to one another to form a six-membered ring, A is a $C_1$- to $C_{20}$-alkylene
which is optionally interrupted by one or more non-adjacent
oxygen atoms,
sulfur atoms, or
functional groups —NR— where the nitrogen atom is optionally protonated or quarternized, —CO—, —CO—O—, —CO—NR—, —SO—, or —SO$_2$—, and
which optionally carries functional groups —COOH or —SO$_3$H, $C_6$- to $C_{20}$-cycloalkylene, $C_6$- to $C_{20}$-arylene which is optionally interrupted by oxygen, sulfur, —NR—, —SO—, or —SO$_2$— and optionally substituted by —COOH or —SO$_3$H, or a mixture of such groups, and n is a number from 5 to 500.

2. The pyrrolidonyl-containing polyester or polyamide of claim 1 wherein A is 1,2-ethylene, 1,2-ethylene incorporated into a piperazine ring, 1,3-propylene, 1,2-propylene, 1,4-butylene, pentamethylene, hexamethylene, octamethylene,

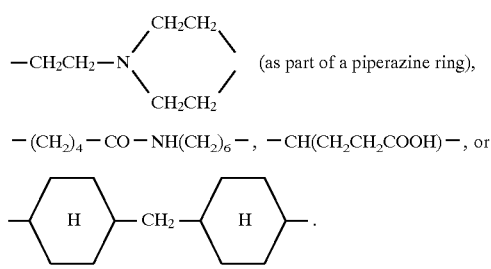

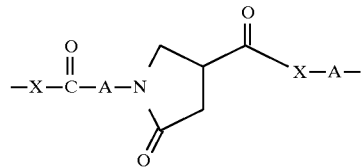

3. A pyrrolidonyl-containing polyester or polyamide containing at least one structural unit of the formula

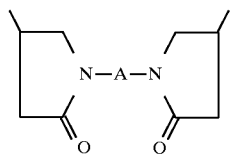

where
X is oxygen or —NR—,
R is hydrogen, $C_1$- to $C_4$-alkyl, or two radicals R are linked to one another to form a six-membered ring, and
A is a $C_1$- to $C_{20}$-alkylene,
which is optionally interrupted by one or more non-adjacent oxygen atoms,
sulfur atoms, or
functional groups —NR—, where the nitrogen atom is optionally protonated or quarternized, —CO—, —CO—O—, —CO—NR—, —SO— or —SO$_2$—, and
which optionally carries functional groups —COOH or —SO$_3$H, $C_6$- to $C_{20}$-cycloalkylene, $C_6$- to $C_{20}$-arylene which is optionally interrupted by oxygen, sulfur, —NR—, —SO—, or —SO$_2$— and optionally carries functional groups —COOH or —SO$_3$H, or a mixture of such groups.

4. A pyrrolidonyl-containing polyurethane or polyurea or a pyrrolidonyl-containing polycarboxylate obtained by reacting
(1) a pyrrolidonyl-containing polyester or polyamide of the formulae V to VII

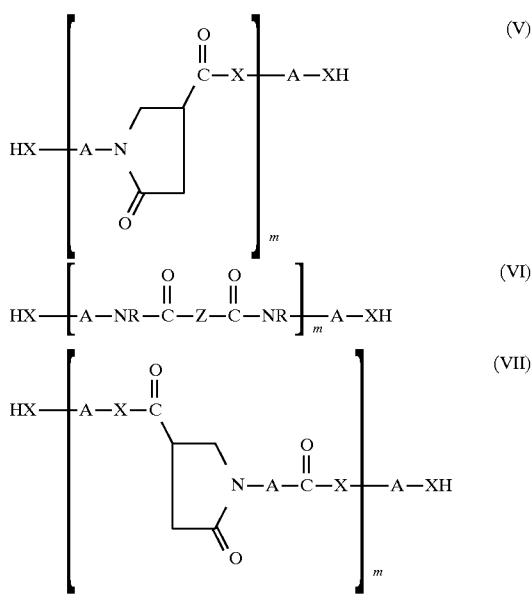

where
R is hydrogen, $C_1$- to $C_4$-alkyl, or two radicals R are linked to one another to form a six-membered ring,
X is oxygen or —NR—,
A is a $C_1$- to $C_{20}$-alkylene,
which is optionally interrupted by one or more non-adjacent
oxygen atoms,
sulfur atoms, or
functional groups —NR— where the nitrogen atom is optionally protonated or quarternized, —CO—, —CO—O—, —CO—NR—, —SO—, or —SO$_2$—, and
which optionally carries functional groups —COOH or —SO$_3$H, $C_6$- to $C_{20}$-cycloalkylene, $C_6$- to $C_{20}$-arylene which is optionally interrupted by oxygen, sulfur, —NR—, —SO—, or —SO$_2$— and optionally carries —COOH or —SO$_3$H, or a mixture of such groups, and Z is a group of the formula VIII

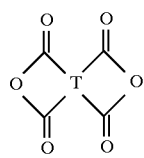

or a mixture of groups of formula VIII with group A and
m is a number from 1 to 50,
with
(2) diisocyanates of the formula OCN—D—NCO, where D is $C_2$- to $C_8$-alkylene, $C_5$- to $C_{10}$-cycloalkylene, phenylene, or $C_1$- to $C_4$-alkylphenylene, or dianhydrides of the formula where T is a tetravalent radical of a $C_2$- to $C_6$-alkane, of a $C_5$- to $C_{10}$-cycloalkane, of benzene, or of naphthalene.

5. An adhesive composition comprising a pyrrolidonyl-containing polyester or polyamide containing at least one structural unit of the formula

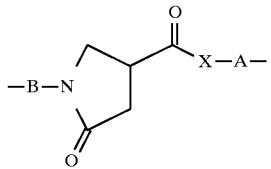

where

X is oxygen or —NR—,

R is hydrogen, $C_1$- to $C_4$-alkyl, or two radicals R are linked to one another to form a six-membered ring, and A is a $C_1$- to $C_{20}$-alkylene,
which is optionally interrupted by one or more non-adjacent
oxygen atoms,
sulfur atoms, or
functional groups —NR—, where the nitrogen atom is optionally protonated or quarternized, —CO—, —CO—O—, —CO—NR—, —SO—, or —$SO_2$—,
which optionally carries functional groups —COOH or —$SO_3H$, $C_6$- to $C_{20}$-cycloalkylene, $C_6$- to $C_{20}$-arylene, which is optionally interrupted by oxygen, sulfur, —NR—, —SO—, or —$SO_2$— and optionally carries functional groups —COOH or —$SO_3H$, or a mixture of such groups, and B is $C_1$- to $C_{20}$-alkylene,
which is optionally interrupted by one or more non-adjacent
oxygen atoms,
sulfur atoms, or
functional groups —NR—, where the nitrogen atom is optionally protonated or quarternized, —CO—, —CO—O—, —CO—NR—, —SO—, or —$SO_2$—, and
which optionally carries functional groups —COOH or —$SO_3H$, $C_6$- to $C_{20}$-cycloalkylene, or a mixture of such groups.

6. A process for the preparation of a pyrrolidonyl-containing polyester or polyamide III as defined in claim 1, which comprises
reacting itaconic acid, itaconic anhydride, an itaconic esters or an itaconyl halide with an aminocarboxylic acid of the formula $H_2N$—A—CO—Y, where Y is OH, O-alkyl or halogen, in a molar ratio of approximately 1:1, and
polycondensing the resultant monomeric pyrrolidone derivative with a diol or diamine of the formula HX—A—XH at elevated temperature.

7. A stabilized aqueous solution of hydrogen peroxide comprising a pyrrolidonyl-containing polyester or polyamide as defined in claim 3 as stabilizing agent.

8. A complex of hydrogen peroxide and a pyrrolidonyl-containing polyester or polyamide as claimed in claim 3.

9. A complex of iodine and a pyrrolidonyl-containing polyester or polyamide as claimed in claim 3.

10. A pharmaceutical preparation comprising a pyrrolidonyl-containing polyester or polyamide as defined in claim 3 as tablet binder or as a constituent of film coatings.

11. A stabilized detergent formulation comprising a pyrrolidonyl-containing polyester or polyamide as defined in claim 3 for enzyme stabilization or for bleach stabilization.

12. A textile comprising a pyrrolidonyl-containing polyester or polyamide as defined in claim 3 as an auxiliary in the production and finishing.

13. A polymer dispersion comprising a pyrrolidonyl-containing polyester or polyamide as defined in claim 3 as a solubilizer or protective colloid in the preparation and stabilization.

14. A hair cosmetic formulation comprising as a film-forming agent and conditioner a pyrrolidonyl-containing polyester or polyamide containing at least one structural unit of the formula as set forth in claim 3.

15. A pyrrolidonyl-containing polyurethane or polyurea or a pyrrolidonyl-containing polycarboxylate obtained by reacting a pyrrolidonyl-containing polyester or polyamide of the formula VII of claim 4 with diisocyanates of the formula OCN—D—NCO, where D is $C_2$- $C_8$-alkylene, $C_5$- to $C_{10}$-cycloalkylene, phenylene or $C_1$- to $C_4$-alkylphenylene, or dianhydrides of the formula

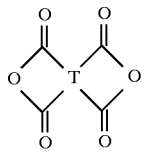

where T is a tetravalent radical of a $C_2$- to $C_6$-alkane, of a $C_5$- to $C_{10}$-cycloalkane, of benzene, or of naphthalene.

* * * * *